United States Patent

Bäckerud

[11] Patent Number: 5,577,545
[45] Date of Patent: Nov. 26, 1996

[54] DETERMINATION OF THE CARBON EQUIVALENT IN STRUCTURE-MODIFIED CAST IRON

[75] Inventor: Stig L. Bäckerud, Katrineholm, Sweden

[73] Assignee: SinterCast AB, Stockholm, Sweden

[21] Appl. No.: 307,708

[22] PCT Filed: Apr. 6, 1993

[86] PCT No.: PCT/SE93/00296

§ 371 Date: Oct. 6, 1994

§ 102(e) Date: Oct. 6, 1994

[87] PCT Pub. No.: WO93/20965

PCT Pub. Date: Oct. 28, 1993

[30] Foreign Application Priority Data

Apr. 9, 1992 [SE] Sweden .................... 9201141

[51] Int. Cl.⁶ .................... B22D 46/00; B22D 27/00; B22D 2/00
[52] U.S. Cl. .................... 164/4.1; 164/58.1; 164/154.1; 164/154.6
[58] Field of Search .................... 164/4.1, 151.4, 164/58.1, 154.6; 73/864.58, 864.53, DIG. 9

[56] References Cited

U.S. PATENT DOCUMENTS

| | | | |
|---|---|---|---|
| 4,667,725 | 5/1987 | Bäckerud | 164/4.1 |
| 4,765,391 | 8/1988 | Bäckerud | 164/4.1 |
| 5,305,815 | 4/1994 | Pan Ping et al. | 164/4.1 |

FOREIGN PATENT DOCUMENTS

| | | |
|---|---|---|
| 1473290 | 4/1969 | Germany . |
| 9113176 | 9/1991 | WIPO . |
| 9206809 | 4/1992 | WIPO . |

Primary Examiner—Jack W. Lavinder
Assistant Examiner—I.-H. Lin
Attorney, Agent, or Firm—Cushman Darby & Cushman, L.L.P.

[57] ABSTRACT

A method for determining the carbon equivalent (C.E.) of structure modified cast iron melts, and use of this method for adjusting the composition of a structure modified cast iron melt. The method is based on the introduction of one or more pieces of iron of low carbon content into a sample container. The iron piece or pieces has/have a size such that the iron piece/pieces will not melt completely when the sample container is filled with melt, which is allowed to solidify. The temperature of the melt is recorded as the melt solidifies. When practicing the method, there is obtained a well-defined absolute temperature as the temperature passes the γ-phase liquidus lines, or a temperature difference in relation to the eutectic temperature of structure-modified cast iron of a closely similar type. The carbon equivalent is determined on the basis of a phase diagram applicable to this structure-modified cast iron. The carbon equivalent of the melt is adjusted by adding carbon and/or silicon or iron of low carbon content.

2 Claims, 2 Drawing Sheets

DETERMINATION OF THE CARBON EQUIVALENT IN STRUCTURE-MODIFIED CAST IRON

BACKGROUND OF THE INVENTION

The present invention relates to a method of determining the carbon equivalent in structure modified cast iron, such as ductile and compacted graphite iron.

The binary phase diagram between iron and carbon is of limited interest in the foundry industry, because all materials which are used to produce cast iron always contain alloying elements such as silicon and manganese, together with impurities such as sulphur and phosphorous, which are able to change the phase relationships. Some of these elements can replace carbon in different proportions, and therewith influence the phase diagram. As a result of the total effect of the substances on the phase diagram, the liquidus temperature found at a specific composition of the melt, referred to as the "carbon equivalent" or C.E., can be expressed as $$C.E.=\% C+\% Si/x+\%P/y+...$$

where x is considered to assume values between 3 and 4 and y is considered to assume values between 3 and 6. In the U.S.A., this equation is normally simplified to $$C.E.=\%C+\%Si/3$$

and this equation is accordingly used below.

This abbreviated formula can be used because the phosphorous content of those melts used within the foundry industry for treated cast iron is very low and therefore unimportant. The area of interest in the manufacture of compacted graphite iron and ductile iron fall within the range of C.E.=3 to 5%.

The majority of published iron-carbon-silicone phase diagrams relate to those conditions under which gray cast iron solidifies, i.e. an untreated iron in which the graphite crystals grow in an extended and branched flaky form. In this system, a eutectic reaction between $\gamma$ (austenite) iron and graphite flakes occurs at C.E. about 4.35% and at a temperature of about 1155° C. Cast iron which has a carbon content or a C.E.<4.35% is normally referred to as being hypo-eutectic, whereas materials which have a carbon content or a C.E. greater than 4.35% are referred to as being hyper-eutectic. As before mentioned, this definition is significant only with regard to flaky gray cast iron.

It is possible to determine the physical C.E. value of hypo-eutectic cast iron by means of the phase change temperature. A cooling curve will show a temperature arrest when the sample temperature passes the liquidus line and $\gamma$ phase begins to precipitate. The reason for this temperature arrest is because the growth kinetics of the austenite phase are very high and because the same also applies to the heat of crystallization of the $\gamma$ phase.

These factors contribute to form a sharp and well-defined point on the temperature-time-curve with the temperature arrest over a given period of time.

This principle has long been used in foundries. For instance, prior publication SE-B-350 124 teaches a device for establishing such a cooling curve for molten iron.

Attempts to use the same technique for the purpose of determining C.E. in hyper-eutectic alloys have not been successful, however. Flaky carbon is the first solid phase to precipitate from such a melt. The carbon crystals, however, will not nucleate immediately after passing the liquidus line, and the latent heat generated is insignificant and is spread over a temperature interval. Consequently, it is impossible to relate changes in the solidification curve to a well-defined phase conversion temperature which would enable C.E. to be determined.

This problem is solved by the method taught by SE-B-342 508. This publication discloses that when the formation of graphite can be suppressed by adding certain elements to the melt, the melt will be undercooled until the corresponding line in the metastable system, $\gamma$-iron and cementite is reached. The first phase that is formed in highly hyper-eutectic melts during solidification will then be cementire, which, due to its high growth kinetics, will release sufficient heat to arrest the temperature decrease for a given period of time. The Applicant of the aforementioned patent publication SE-B-342 508 does not appear to be concerned about the fact that two completely different melts, the one hypo-eutectic with primary $\gamma$-phase precipitation and the other hyper-eutectic precipitation of primarily cementite, will give the same result. The applicants in those prior art documents have also thus ignored the very important area of $\gamma$liquidus displacement between the stable and metastable states. The applicant of the aforesaid patent publication SE-B-342508 also maintains that certain elements will suppress the formation of graphite and that tellurium, boron and cerium would appear to be the most effective elements, although magnesium is also mentioned in this context. Although this statement is partially true, millions of tonnes of ductile iron are produced annually with limited additions of cerium (and other rare earth metals and magnesium), with only a slight risk of cementite formation.

SUMMARY OF THE INVENTION

A study of modified cast iron (i.e. subsequent to the addition of rare earth metals and/or magnesium) has shown that these types of iron must be described with a completely different phase diagram, where both the $\gamma$-liquidus line and the liquidus line of modified graphite nodules, C.E. and the temperature at the eutectic reaction are displaced.

The invention relates to a method for determining the carbon equivalent (C.E.) of structure modified cast iron melts, and to the use of this method for adjusting the composition of a structure modified cast iron melt. The method is based on the introduction of one or more pieces of iron of low carbon content into a sample container. The iron piece or pieces has/have a size such that the iron piece/pieces will not melt completely when the sample container is filled with melt, which is allowed to solidify. The temperature of the melt is recorded as the melt solidifies. When practicing the method, there is obtained a well-defined absolute temperature as the temperature passes the $\gamma$-phase liquidus lines, or a temperature difference in relation to the eutectic temperature of structure modified cast iron of a closely similar type. The carbon equivalent is determined on the basis of a phase diagram applicable to this structure modified cast iron. The carbon equivalent of the melt is adjusted by adding carbon and/or silicon or iron of low carbon content.

BRIEF DESCRIPTION OF THE DRAWING

The invention will now be described in more detail with reference to the accompanying drawings, in which.

DETAILED DESCRIPTION

Figure 1:
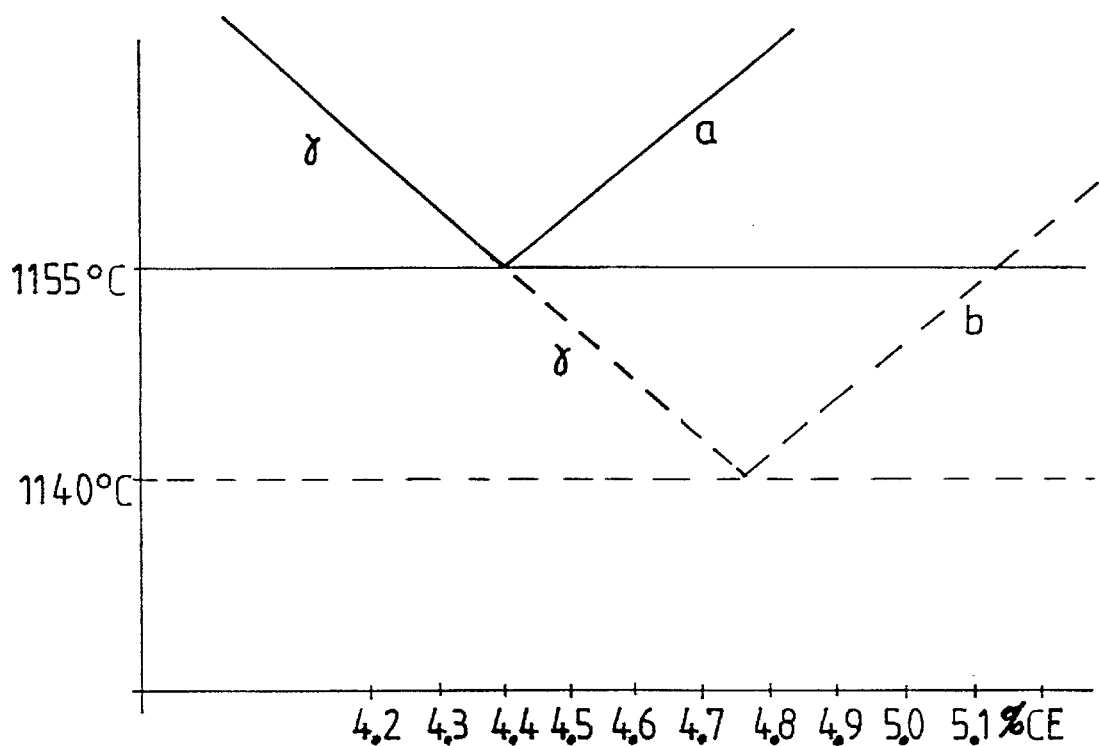
FIG 1 illustrates the area around the eutectic reaction in a phase diagram relating to modified cast iron.

FIG. 1 illustrates the change from the normal iron-carbon-silicone-phase diagram to a case with ductile iron with a nucleation level of 100±50 nodules mm$^{-2}$ in a test bar having a diameter of 2.5 cm. Line b corresponds to a phase diagram applicable to structure-modified cast iron, and line a corresponds to non-structure-modified cast iron. The eutectic composition was found to be a C.E. of about 4.7 and the temperature at eutectic solidification was found to be about 1140° C. At this point, γ-iron and graphite nodules precipitated in accordance with the lever rule. At lower C.E. values, the gamma phase develops essentially in dendritic forms, while above C.E. about 4.7% graphite nodules may precipitate primarily from the melt, these nodules tending to rise to upper parts of the melt (flotation).

This inoculation level of 100±50 nodules mm$^{-2}$ is chosen because, in the majority of cases, it represents the actual state of a ductile iron melt after base treatment (i.e. after adding such substances as FeSiMg and FeSi and optionally a given amount of rare earth metals).

When this level has been reached in a melt, it is possible to determine to a high degree of accuracy the amount of inoculation agent required in order to obtain the level for the quantity of nodules desired (or the number of nodules per unit surface). The residual magnesium content in this type of iron must exceed 0.020 percent by weight.

It is most desirable for the foundry industry to produce cast products which have a composition just below the dynamic displaced eutectic point. In this region, for example between C.E.=4.55 to 4.65%, solidification begins with the precipitation of a fine dendritic network throughout the whole of the cast product. This network provides a certain degree of stability to the cast product and prevents the graphite nodules formed in a later stage of the process from floating up in the melt. This fine dendritic network does not seriously limit the interdendritic flow of the melt, thereby reducing the risk to form porosities and shrinkage.

A reliable method of controlling the actual C.E. within such narrow limits during the process would be of great value to the foundry industry. None of the earlier known methods will produce the results desired, either due to lack of accuracy or because they cannot be applied to structure modified cast iron due to undesired carbide formation which will mask essential information. In accordance with the present invention, it has been found that a sample taken for thermal analysis and for obtaining information concerning the crystallization properties of structure modified melts, as described in more detail in the prior publication U.S. Pat. No. 4,667,725 can also be used to determine the physical C.E. of compact graphitic cast iron and ductile iron in melts which have a C.E. value up to the actual eutectic point, i.e. in the above case a C.E. of 4.7%, subsequent to taking certain further measures.

The method according to Patent Specification U.S. Pat. No. 4,667,725, is based on taking a sample from the iron melt concerned in a container which has been preheated or heated by imersion in the melt and which is equipped with two temperature sensors, such as thermocouples for instance, one placed close to the inner wall of the container and the other placed in the centre of the container approximately equidistant from the nearest outer walls.

When a sample container of this kind is used, it is normally possible to observe the growth of gamma dendrites as a more or less clearly indicated decrease in the solidification rate at the centre of the sample. This method is similar to known techniques for determining the precise amount of C.E. in the type of materials concerned. It has been found, however, that such methods, which are taught, for instance in SE-B-342 508, do not solve the problem upon which the present invention is based.

In accordance with the present invention, it has been found that this problem can be solved by triggering nucleation and the onset of the precipitation of the γ-phase with a mechanism which will constantly guarantee that a thermal signal can be obtained precisely when the temperature of the sample crosses the liquidus line in the phase diagram concerned.

This mechanism can be obtained by supplying one or more pieces of pure iron in contact with the melt in the sample container. The iron piece or pieces used in this respect shall contain so little iron as not to substantially affect the average composition of the sample as a whole, although sufficient so as not to melt completely and be mixed in the sample volume as the sample container is filled and during subsequent cooling of the sample. This means, in practice, that a small amount of relatively pure iron will be present in the sample. During the cooling process, these small amounts of iron will crystallize at a much higher temperature than the liquidus temperature of the γ-phase, as calculated on the average composition of the sample. Consequently, a small γ-phase crystal will already have formed when the temperature passes the γ-phase liquidus line in the system used, representing the composition of the major part of the sample.

It is necessary that the cooling in the interior of the sample be delayed in relation to that at the container wall and that the sample container be placed in the bulk volume of the melt to avoid transient surface reactions, which normally occur at the wall and extend 2 or 3 mm in the bulk volume.

Alternatively, the heat transport through the sample container wall can be lowered by thermal isolation of a limited part of the wall, which then by itself can be produced of a low carbon steel or a piece of iron be attached directly to such isolated point of the wall.

At this point in time, γ-dendrites can immediately begin to develop throughout the entire sample sample volume. The start of this first development of γ-phase dendrites is manifested by a clear bend in the solidification curve taken in the centre of the sample volume. This curve, which is seen most clearly in the derivative of the temperature-time-curve, can be referred to as the γ-function. This temperature can be related as the absolute temperature (in °C.) to the actual liquidus temperature, or may be calibrated in relation to chemical analysis of a number of samples.

Figure 2A:
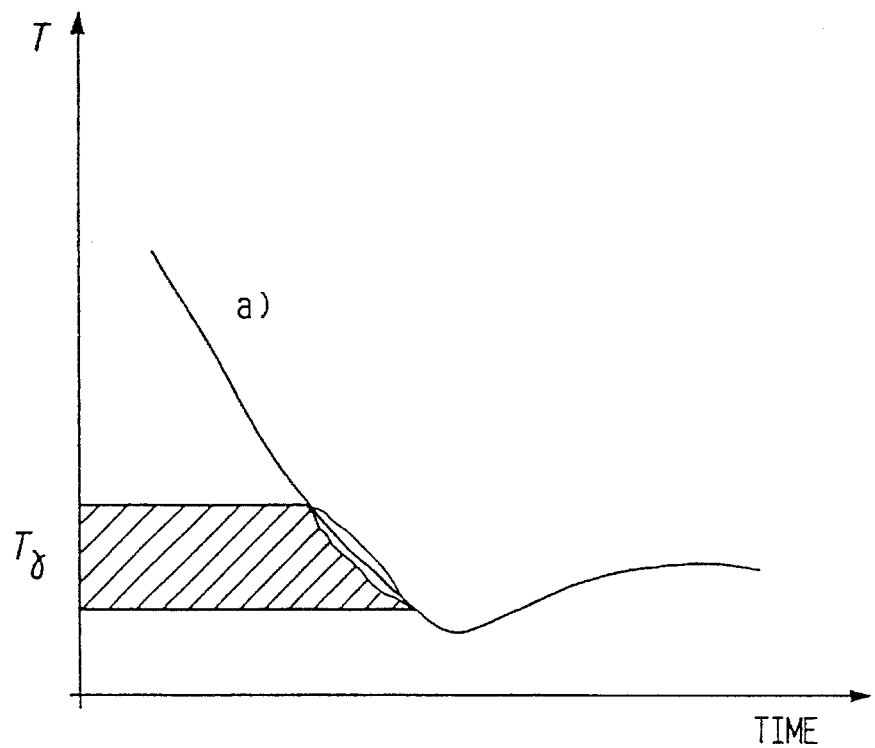
FIG. 2(a) and 2(b) illustrate solidification curves, in accordance with previously known techniques and also in accordance with the invention.
Figure 2B:
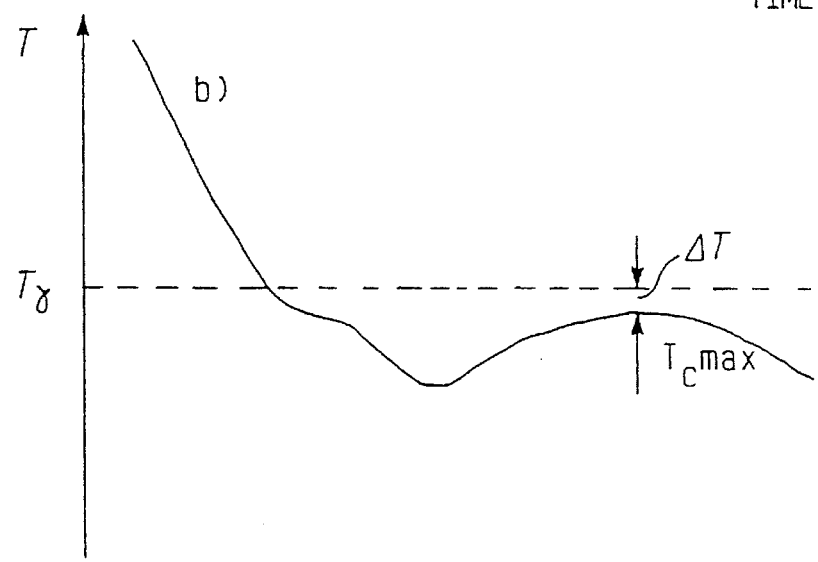

It is of still greater interest, however, to place the commencement of the growth of the γ-phase in relation to the steady state temperature during the eutectic reaction that immediately follows the dendrite development during the solidification process. FIG. 2(a) and 2(b) illustrate the invention and shows solidification curves obtained from centrally positioned temperature sensors in case a) showing γ-dendrite growth without the use of a triggering agent consisting of pure iron. It will be seen from FIG. 2 that dendrite growth begins sometime during the hatched region of the Figure, at about Tγ. When a triggering agent is used, Tγ can be identified as a determined temperature. More preferably, the difference between Tγ and $T_c$ max. can be used, this difference being given in the Figure as ΔT. This enables a relationship between the temperature and the time from the commencement of dendrite growth to the eutectic reaction to be obtained directly. This will provide a better picture of the progress of the solidification process when casting structure modified iron, and the method also enables the carbon equivalent to be established to a high degree of accuracy.

Thus, subsequent to having obtained the values from a solidification sample and with the aid of the actual value of Tγ or ΔT when $T_c$ max. is established, it is possible to establish the actual temperature of Tγ and therewith also C.E. of the melt with the aid of the iron-carbon-silicone diagram with displaced values depending on the alloy additions to the melt concerned. FIG. 1 thus shows a diagram b) relating to ductile iron having 100±50 nodules per $mm^2$ in a sample rod of 2.5 cm diameter. Thus, if the temperature Tγ is 1150° C. or/delta/T=10° K., C. E. can be calculated to 4.52% in this particular case, with the aid of FIG. 1.

A final adjustment of the inoculation properties is obtained by making a further addition of ferrosilicon (Fe+ 75% Si). This silicon addition, however, will result in an increase in the final C.E. in the cast material, which must be taken into account when calculating C.E.

For instance, if 0.16% Fe-75% Si is added subsequent to determining C.E., C.E. will be increased by +0.04%, as will readily be seen from the following equations:

$$\frac{75\% \cdot 0.16}{100} = 0.12\% \text{ Si which gives } \frac{0.12\% \text{ Si}}{3} = 0.04\% \text{ C.E.}$$

The present invention thus constitutes an essential improvement on the technique described in U.S. Pat. No. 4,667,725. This patent teaches similar sampling procedures and procedures for controlling the inherent crystallization properties of cast iron melts, such as degree of modification and the number of crystallization nucleants. It has not earlier been possible to simultaneously obtain knowledge of the carbon equivalent in a reproducible manner, and still less possible to measure the carbon equivalent in a manner which will enable a current or prevailing value to be obtained within a short period of time which will enable the carbon equivalent to be adjusted prior to casting the melt.

I claim:

1. A method for determining the carbon equivalent of a structure-modified cast iron melt, comprising:

(a) providing measured and calibrated values of the eutectic temperature for structure-modified cast iron having a closely similar type to that of said melt, and providing from said values a phase diagram applicable to said closely similar type of structure-modified cast iron;

(b) providing a sample container having a defining wall and having a centrally positioned temperature sensor, and causing the sample container to become in thermal equilibrium with the melt;

(c) taking a sample of the melt into the sample container;

(d) providing the sample container with one or more pieces of iron of low carbon content in contact with the iron melt sample in the sample container, said piece or pieces having a size such that said piece or pieces will not melt completely nor substantially affect the average composition of said sample as said sample solidifies in said sample container, while cooling in said sample is delayed at said sample container wall;

(e) allowing the sample in the sample container to solidify, while recording temperature as sensed by said sensor, in relation to time; and (f) recording the temperature as sensed by said sensor, for the passage of the γ-phase liquidus line as an absolute temperature or as a temperature difference in relation to said measured and calibrated values, and using said absolute temperature or temperature difference to determine the carbon equivalent for the structure-modified cast iron of said melt from said phase diagram.

2. The method of claim 1, further including:

(g) on the basis of the carbon equivalent determined in step (f), adding carbon and/or silicon or iron of low carbon content to the melt, for thereby adjusting the carbon equivalent of the melt.

* * * * *